United States Patent [19]

Walsh

[11] 4,333,951
[45] Jun. 8, 1982

[54] 2-AMINO-6-BIPHENYLACETIC ACIDS

[75] Inventor: David A. Walsh, Richmond, Va.

[73] Assignee: A. H. Robins Company, Inc., Richmond, Va.

[21] Appl. No.: 165,323

[22] Filed: Jul. 2, 1980

Related U.S. Application Data

[63] Continuation-in-part of Ser. No. 57,118, is a continuation-in-part of Ser. No. 851,641, Nov. 15, 1977, abandoned.

[51] Int. Cl.³ ............... C07C 101/447; A61K 31/195; A61K 31/215
[52] U.S. Cl. .................... 424/319; 424/309; 562/456; 562/457; 562/452; 560/47; 560/45; 560/48
[58] Field of Search ............... 562/433, 449, 456, 457, 562/451, 452; 560/19, 47, 48, 45; 424/309, 319

[56] References Cited

U.S. PATENT DOCUMENTS

| | | | |
|---|---|---|---|
| 3,452,079 | 6/1969 | Shen et al. | 562/433 |
| 3,457,300 | 7/1969 | Dorn et al. | 562/433 |
| 3,624,142 | 11/1971 | Shen et al. | 562/433 |
| 3,784,704 | 1/1974 | Cohen et al. | 424/317 |
| 3,821,268 | 6/1974 | Diamond et al. | 562/449 |
| 3,966,978 | 6/1976 | Elenbogen et al. | 424/317 |
| 4,021,479 | 5/1977 | Seeger et al. | 562/449 |

FOREIGN PATENT DOCUMENTS 8226  2/1980  European Pat. Off. .............. 560/48

Primary Examiner—Natalie Trousof
Assistant Examiner—James H. Reamer

[57] ABSTRACT

Novel 2-amino-6-biphenylacetic acids, esters, and metal salts are provided of the formula:

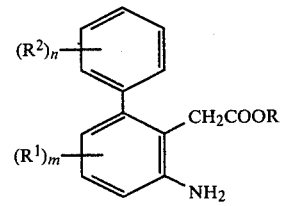

wherein R represents hydrogen or lower alkyl, $R^1$ represents fluoro, chloro, bromo, lower-alkyl or amino; $R^2$ represents lower-alkyl, lower-alkoxy, fluoro, chloro, bromo, amino or trifluoromethyl; n is 0–3 and m is 0–2, and the pharmaceutically acceptable salts thereof. The compounds exhibit muscle relaxant activity, and are also useful as anti-inflammatory agents.

12 Claims, No Drawings

2-AMINO-6-BIPHENYLACETIC ACIDS

REFERENCE TO PARENT PATENT APPLICATIONS

This application is a continuation-in-part of U.S. patent application Ser. No. 057,118 filed July 12, 1979, which is a continuation-in-part of U.S. patent application Ser. No. 851,641 filed Nov. 15, 1977, both now abandoned.

BACKGROUND OF THE INVENTION

The present invention relates to novel biphenylacetic acids and is more particularly concerned with certain 2-amino-6-biphenylacetic acids, esters, and metal salts, compositions thereof, methods for the production thereof and use of the same.

Various biphenylacetic acids have been demonstrated to possess anti-inflammatory activity as disclosed in U.S. Pat. Nos. 3,784,704 and 3,966,978. Biphenylacetic acids and esters having an amino substituent in the phenyl ring to which is attached the acetic acid moiety are disclosed in French Pat. No. M 5,737. German Offenlegungsschrift No. 2,355,084 discloses methyl 3-amino-4-biphenylacetate as an intermediate in the preparation of phenanthridones.

OBJECTS AND SUMMARY OF THE INVENTION

It is an object of the present invention to provide novel 2-amino-6-biphenylacetic acids, esters, and metal salts and to provide methods for the preparation of such novel compounds.

It is another object of the present invention to provide a method for using the novel compounds of the present invention for treatment of a living animal body, especially mammalian bodies, to provide muscle relaxation as well as inhibit inflammation.

It is yet another object of the present invention to provide novel compositions comprising the novel compounds of the present invention.

In one aspect of the present invention there is provided a compound selected from the group having the formula:

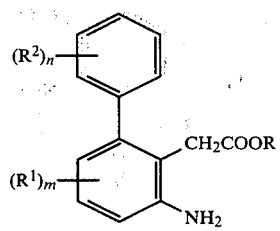

Formula I wherein:
R is hydrogen or lower alkyl,
R$^1$ is fluoro, chloro, bromo, lower alkyl, or amino,
R$^2$ is lower alkyl, lower alkoxy, fluoro, chloro, bromo, amino, or trifluoromethyl,
n is 0–3 and m is 0–2,
and the pharmaceutically acceptable salts thereof.

In another aspect of the present invention there is provided a therapeutic composition suitable for providing muscle relaxation comprising (a) an effective amount of a compound selected from the group having the formula as defined above as Formula I and (b) a pharmaceutically acceptable carrier therefor.

In yet another aspect of the present invention there is provided a method for providing muscle relaxation in a living animal body with a minimum of undesirable side effects comprising internally administering to said living animal body an effective amount of a compound selected from the group having the formula as defined above as Formula I.

In still yet another aspect of the present invention there is provided a therapeutic composition suitable for alleviating inflammation comprising (a) an effective amount of a compound selected from the group having the formula defined above as Formula I, and (b) a pharmaceutically acceptable carrier therefor.

In still another aspect of the present invention there is provided a method for alleviating inflammation in a living animal body with a minimum of undesirable side effects comprising internally administering to said living animal body an effective amount of a compound selected from the group having the formula defined above as Formula I, and (b) a pharmaceutically acceptable carrier therefor.

DETAILED DESCRIPTION OF THE INVENTION

The novel compounds of this invention are useful as muscle relaxant and anti-inflammatory agents. The compounds may be administered alone or with suitable pharmaceutical carriers to warm blooded animals, mammals such as felines, canines and humans and can be in solid or liquid form as, for example, tablets, capsules, powders, solutions, suspensions or emulsions.

The compounds can be administered orally, parenterally, subcutaneously or intramuscularly. The unit dosage form can contain from about 1 to about 100 milligrams of a novel compound of this invention and can be administered in multiples thereof up to a daily dosage level of about 500 milligrams.

The solid unit dosage form can be a gelatin capsule containing a novel compound of this invention and a pharmaceutically acceptable filler or carrier such as sucrose, lactose, corn starch and the like. Tablets containing the novel compounds represent another embodiment of this invention and are prepared using conventional tableting materials.

The novel concept of the present invention resides in the provision of therapeutically active 6-biphenylacetic acids, esters and metal salts which have a primary amino group ortho to the acetic acid group. Therapeutically active compounds possessing such an arrangement have been heretofore unknown prior to the present invention.

The anti-inflammatory utility of the novel compounds of this invention was determined using a modification of the Evans Blue-Carrageenan Pleural Effusion Assay of Sancilio, L. F., J. Pharmacol. Exp. Ther. 168, 199–204 (1969).

The muscle relaxant utility of the novel compounds of the present invention was determined using the loss of righting test as set forth by A. P. Roszkowski, J. Pharmacol. and Expt. Therapeutics, Vol 129, page 75 (1960).

It has been surprisingly and unexpectedly found that the 2-amino-6-biphenylacetic acids of the present invention exhibit significant muscle relaxant activity, while 2-aminobiphenylacetic acids having the phenyl substituent in the 3 and 5 positions exhibit no such activity. The surprising muscle relaxant properties of the 2-amino-6-biphenylacetic acids is clearly shown in the following Table.

TABLE I

| Substituent | Dose (mg/kg) | Percent Loss of Righting Reflex |
|---|---|---|
| 3-phenyl | 250 | 0 |
| 5-phenyl | 100 | 0 |
| 6-phenyl | 100 | 100 |
| 6-phenyl | 50 | 0 |

In the definition of symbols in the formulae hereof and where they appear elsewhere throughout this specification, the terms have the following significance.

The term "lower alkyl" as used herein includes straight and branched chain radicals of up to six carbon atoms inclusive, preferably no more than four carbon atoms, and is exemplified by such groups as methyl, ethyl, propyl, isopropyl, butyl, sec. butyl, tertiary butyl, amyl, isoamyl and hexyl. The term "lower alkoxy" has the formula -O-lower alkyl.

When $m=2$ or $n=2$ or 3, $R^1$ or $R^2$ can be the same or different radicals.

Illustrative of pharmaceutically acceptable salts are sodium, potassium, calcium, magnesium, zinc, copper, and the hydrates thereof.

METHOD OF PREPARATION

The compounds of Formula I wherein R represents hydrogen may be prepared by hydrolysis of 4-phenylindolin-2-ones (II) in aqueous basic solution followed by neutralization of the basic reaction mixture with a suitable organic acid such as acetic acid or a dilute mineral acid as indicated by the following:

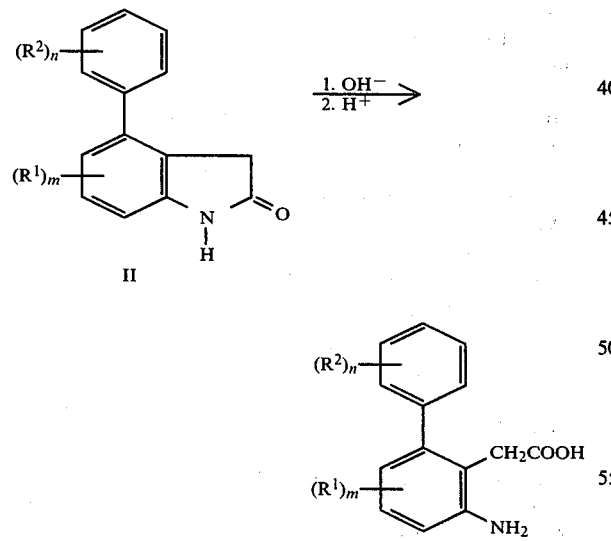

wherein $R^1$ and $R^2$ are as defined hereinabove.

The hydrolysis of a 4-phenylindolin-2-one (II) is carried out in a dilute aqueous base as, for example, a 3 N sodium hydroxide solution, for a period of from about 1.0 to about 60 hours, usually until the indolin-2-one has dissolved. The hydrolysis may be run in an inert atmosphere using nitrogen. The hydrolysis mixture may be filtered to remove base-insoluble materials and the pH of the basic solution is adjusted to a pH of from 6-7 by the addition of a weak organic acid such as glacial acetic acid or a dilute mineral acid such as hydrochloric acid.

The free acids can contain water of crystallization. Therefore the free acids containing various degrees of hydration are included within the scope of the invention.

The lower alkyl esters of Formula I are preferably prepared from the acids which are converted to an alkali metal salt, preferably the sodium or potassium salt which is isolated, dried, and then reacted in a suitable solvent as for example, dimethyl formamide, with an alkali halide, preferably an alkyl iodide, to furnish the desired ester.

The 4-phenylindolin-2-ones (II) are prepared from appropriately substituted biphenylamines (V) by the following reaction sequence, wherein $R^1$ and $R^2$ have the values hereinabove defined except additionally $R^1$ and $R^2$ may be nitro in Formulas III, IV and V, and R is lower alkyl, preferably ethyl. The reaction conditions employed are more fully set forth hereinafter in the specific preparations which follow.

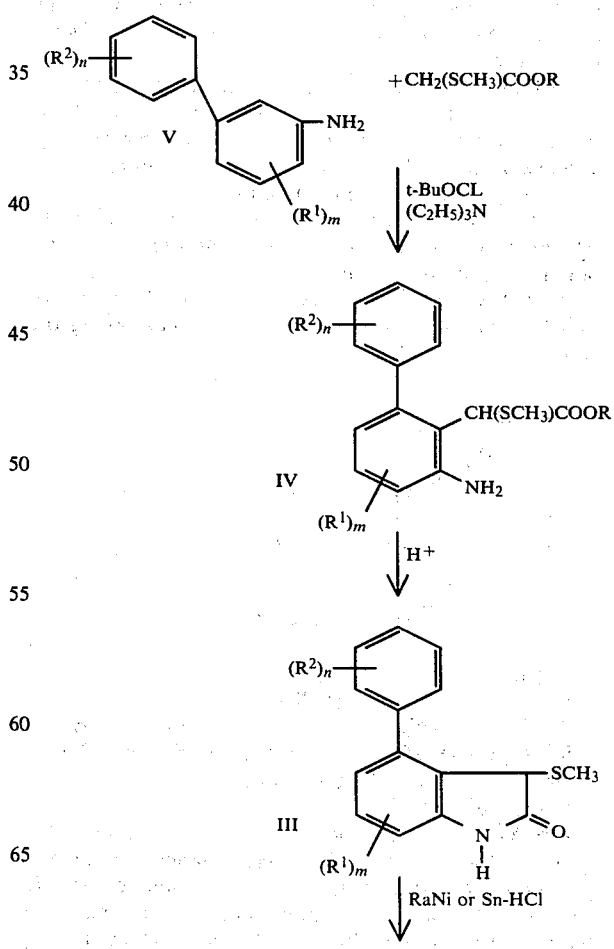

-continued

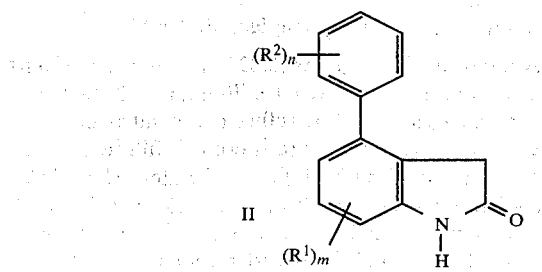

Compounds of Formula II wherein $R^1$ or $R^2$ is $NH_2$, are prepared from the corresponding biphenyl amine wherein $R^1$ or $R^2$ is $NO_2$, the resulting $NO_2$ radical in Formula III being reduced by RaNi or Sn/HCl at the same time as the methylthio group is removed. Additional reducing agent is required and in the instance of tin, three additional moles per mole of $NO_2$ are required as well as sufficient HCl to maintain acid conditions.

Preparation 1

3-Methylthio-4-phenylindolin-2-one m-Biphenylamine hydrochloride (35.3 grams, 0.172 mole) is partitioned between 300 milliters of methylene chloride and 200 ml. of 5% sodium hydroxide solution. The layers are separated and the methylene chloride layer is dried (sodium sulfate) and its volume adjusted to 400 milliliters with additional methylene chloride. The solution is cooled to −65° C. and 23.0 grams (0.172 mole) of ethyl 2-methylthioacetate are added. Immediately, 18.9 grams (0.175 mole) of t-butylhypochlorite are added dropwise. After the addition is completed, the mixture is stirred at −65° C. for 1.5 hours, treated with 17.2 grams (0.125 mole) of triethylamine and allowed to warm to ambient temperature. The methylene chloride solution is washed twice with two 100 milliliter portions of water, concentrated, and the residue dissolved in 200 milliliters of methanol. This solution is heated to reflux, treated with 40 milliliters of 3 N hydrochloric acid and the mixture heated at reflux overnight. The dark solution is concentrated to approximately 100 milliliters when a solid begins to precipitate. The mixture is cooled, the solid collected by filtration, washed with a small volume of cold methanol and dried to give 22.8 grams (52%) of yellow material. A nuclear magnetic resonance analysis of the material indicates that the solid is a mixture of the 4-phenyl isomer and the 6-phenyl isomer in a ratio of 2:1. The 4-phenyl isomer is separated from the 6-phenyl isomer by fractional crystallization from benzene. Three recrystallizations of the yellow solid from benzene give 8.5 grams (19%) of 3-methylthio-4-phenylindolin-2-one as a white solid, m.p. 182°–5° C.

Analysis: Calculated for $C_{15}H_{13}NOS$: C, 70.56; H, 5.13; N, 5.49. Found: C, 70.26; H, 5.16; N, 5.14.

Preparation 2

4-Phenylindolin-2-one

A stirring solution of 3.5 grams (0.014 mole) of 4-phenyl-3-methylthioindolin-2-one in 75 milliliters of tetrahydrofuran is treated portionwise with 20 grams of a commercial Raney nickel/water suspension. The mixture is filtered through Celite and the filtrate concentrated to give a yellow solid. This solid is recrystallized from benzene to yield 1.6 grams (57%) of product as an off-white solid. An analytical sample was prepared from isopropanol; m.p. 192°–194° C.

Analysis: Calculated for $C_{14}H_{11}NO$: C, 80.36; H, 5.30; N, 6.69. Found: C, 80.52; H, 5.41; N, 6.72.

Preparation 3

3-Methylthio-7-methyl-4-phenylindolin-2-one

A solution of 30.6 grams (0.13 mole) of 3-amino-4-methylbiphenyl in 400 milliliters of methylene chloride is cooled to −65° C. and treated with 17.0 grams (0.13 mole) of ethyl 2-methylthioacetate and then 14.2 grams (0.132 mole) of t-butylhypochlorite while maintaining the temperature below −60° C. The reaction mixture is stirred at −65° C. for 1.5 hours, treated with 13.3 grams (0.132 mole) of triethyl amine and allowed to warm to ambient temperature. The solution is washed twice with water and concentrated. The residue is dissolved in 200 milliliters of methanol, 40 milliliters of 3 N hydrochloric acid are added, and the mixture refluxed overnight. The solution is concentrated until a solid begins to precipitate. The mixture is cooled, and the solid collected by filtration.

Preparation 4

When in the procedure of Preparation 3 and in the manner of the preceding discussion, 3-amino-4-methylbiphenyl is replaced by equal molar amounts of the following:

3-amino-5-methylbiphenyl,
3-amino-2'-methoxybiphenyl,
3-amino-2',5'dimethoxybiphenyl,
3-amino-3'-chlorobiphenyl,
3-amino-3',5'-dibromobiphenyl,
3-amino-4-chlorobiphenyl,
3-amino-4,6-dichlorobiphenyl,
3-amino-6-methyl-2'-methylbiphenyl,
3-amino-2',4-dichlorobiphenyl,
there are obtained
3-methylthio-6-methyl-4-phenylindolin-2-one and 3-methylthio-4-methyl-6-phenylindolin-2-one,
3-methylthio-4-(2-methoxyphenyl)indolin-2-one and 3-methylthio-6-(2-methoxyphenyl)indolin-2-one,
3-methylthio-4-(2,5-dimethoxyphenyl)indolin-2-one and 3-methylthio-6-(2,5-dimethoxyphenyl)indolin-2-one,
3-methylthio-4-(3-chlorophenyl)indolin-2-one and 3-methylthio-6-(3-chlorophenyl)indolin-2-one,
3-methylthio-4-(3,5-dibromophenyl)indolin-2-one and 3-methylthio-6-(3,5-dibromophenyl)indolin-2-one,
3-methylthio-7-chloro-4-phenylindolin-2-one,
3-methylthio-5,7-dichloro-4-phenylindolin-2-one, 3-methylthio-5-methyl-4-(2-methylphenyl)indolin-2-one, and
3-methylthio-7-chloro-4-(2-chlorophenyl)indolin-2-one.

Preparation 5

6-Methyl-4-phenylindolin-2-one.

To a slurry of 11.8 grams (0.044 mole) of 3-methylthio-6-methyl-4-phenylindoline-2-one in 500 milliliters of tetrahydrofuran are added 100 grams of a commercial Raney nickel/water preparation portionwise over a two-hour period. The mixture is filtered through Celite and the filtrate concentrated. A small amount of methylene chloride is added to the residue and the resulting solid is collected by filtration.

Preparation 6

When in the procedure of Preparation 5 and in the manner of the preceding discussion, 3-methylthio-6-methyl-4-phenylindolin-2-one is replaced by equal molar amounts of the following methylthioindolin-2-ones:
3-methylthio-7-methyl-4-phenylindolin-2-one,
3-methylthio-6-methyl-4-phenylindolin-2-one,
3-methylthio-4-(2-methoxyphenyl)indolin-2-one,
3-methylthio-4-(2,5-dimethoxyphenyl)indolin-2-one,
3-methylthio-4-(3-chlorophenyl)indolin-2-one,
3-methylthio-4-(3,5-dibromophenyl)indolin-2-one,
3-methylthio-7-chloro-4-phenylindolin-2-one,
3-methylthio-5,7-dichloro-4-phenylindolin-2-one,
3-methylthio-4-(2-methylphenyl)indolin-2-one, and
3-methylthio-7-chloro-4-(2-chlorophenyl)indolin-2-one,
there are obtained
7-methyl-4-phenylindolin-2-one,
6-methyl-4-phenylindolin-2-one,
4-(2-methoxyphenyl)indolin-2-one,
4-(2,5-dimethoxyphenyl)indolin-2-one,
4-(3-chlorophenyl)indolin-2-one,
4-(3,5-dibromophenyl)indolin-2-one,
7-chloro-4-phenylindolin-2-one,
5,7-dichloro-4-phenylindolin-2-one,
5-methyl-4-(2-methylphenyl)indolin-2-one, and
7-chloro-4-(2-chlorophenyl)indolin-2-one.

Preparation 7

When in the procedure of Preparation 3 and in the manner of the preceding discussion, 3-amino-4-methylbiphenyl is replaced by equal molar amounts of the following nitro derivatives:
3-amino-3'-nitrobiphenyl,
3-amino-2'-nitrobiphenyl,
3-amino-4,6-dinitrobiphenyl,
there are obtained,
3-methylthio-4-(3-nitrophenyl)indolin-2-one, and 3-methylthio-6-(3-nitrophenyl)indolin-2-one,
3-methylthio-4-(2-nitrophenyl)indolin-2-one, and 3-methylthio-6-(2-nitrophenyl)indolin-2-one,
3-methylthio-4-phenyl-5,7-dinitroindolin-2-one.

Preparation 8

4-Phenyl-5,7-diaminoindolin-2-one

A mixture of 4.9 grams (0.014 mole) of 3-methylthio-4-phenyl-5,7-dinitroindolin-2-one, 4.2 grams (0.035 mole) of tin powder, 10 milliliters of concentrated hydrochloric acid and 50 milliliters of ethanol are refluxed for 4 hours under nitrogen. The hot mixture is filtered and the filtrate concentrated to give a solid.

Preparation 9

When in the procedure of Preparation 8 and in the manner of the preceding discussion, 3-methylthio-4-phenyl-5,7-dinitroindolin-2-one is replaced by equal molar amounts of the following nitro-methylthioindolins of Preparation 7:
3-methylthio-4-(3-nitrophenyl)indolin-2-one,
3-methylthio-4-(2-nitrophenyl)indolin-2-one,
there are obtained
4-(3-aminophenyl)indolin-2-one, and
4-(2-aminophenyl)indolin-2-one.

EXAMPLE 1

2-Amino-3-methyl-6-biphenylacetic Acid Hydrate (1:4)

A mixture of 4.79 grams (0.0215 mole) of 7-methyl-4-phenylindolin-2-one and 60 milliliters of 3 N sodium hydroxide was heated at reflux under nitrogen for 17 hours. The reaction mixture is cooled, filtered, and the filtrate diluted with 60 milliliters of water. The solution is cooled, made acidic with glacial acid and the resulting solid immediately collected by filtration, washed with cold water and dried under vacuum.

EXAMPLE 2

2-Amino-6-biphenylacetic Acid

A mixture of 1.5 grams (0.007 mole) of 4-phenylindolin-2-one and 20 milliliters of 3 N sodium hydroxide is heated at reflux for 6 hours. The mixture is cooled and filtered. The filtrate is made acidic with glacial acetic acid, and the resulting solid collected by filtration, washed with water and dried to yield 0.5 grams (32%) of product as a tan powder, m.p. 190°–191° C. (dec.).

Analysis: Calculated for $C_{14}H_{13}NO_2$: C,73.99; H,5.77; N,6.16. Found: C,73.54; H,5.71; N,6.28.

EXAMPLE 3

Sodium 2-amino-6-biphenylacetate

A solution of 2.8 grams (0.0125 mole) of crude 2-amino-6-biphenylacetic acid in 40 milliliters of tetrahydrofuran is treated with 2 milliliters of 5% sodium hydroxide. The solution is concentrated and the residue subjected to a benzene azetrope to eliminate water. The resulting tan solid is recrystallized three times from ethyl alcohol to give a pure sample of the sodium salt as a tan solid, m.p. 128°–48° C. (dec.).

Analysis: Calculated for $C_{14}H_{12}NaNO_2$: C,67.46; H,4.85; N,5.62. Found: C,67.25; H,4.96; N,5.65.

EXAMPLE 4

When in the procedure of Example 1 and in the manner of the preceding discussion, 7-methyl-4-phenylindolin-2-one is replaced by equal molar amounts of
5-methyl-4-(2-methylphenyl)indolin-2-one,
there is obtained
2-amino-5,2'-dimethyl-6-biphenylacetic acid.

EXAMPLE 5

When in the procedure of Example 1 and in the manner of the preceding discussion, 7-methyl-4-phenylindolin-2-one is replaced by equal molar amounts of
4-(2-methoxyphenyl)indolin-2-one,
4-(2,5-dimethoxyphenyl)indolin-2-one,
there are obtained
2-amino-2'-methoxy-6-biphenylacetic acid,
2-amino-2',5'-dimethoxy-6-biphenylacetic acid.

EXAMPLE 6

When in the manner of Example 1 and in the manner of the preceding discussion, 7-methyl-4-phenylindolin-2-one is replaced by equal molar amounts of
4-(3,5-dibromophenyl)indolin-2-one,
7-chloro-4-(2-chlorophenyl)indolin-2-one,
there are obtained
2-amino-3',5'-dibromo-6-biphenylacetic acid,
2-amino-2',3-dichloro-6-biphenylacetic acid.

EXAMPLE 7

When in the procedure of Example 1, 2-moles of potassium hydroxide per mole of the indolin-2-one is substituted for the sodium hydroxide, ethanol is substituted for water and 7-methyl-4-phenylindolin-2-one is replaced by equal molar amounts of
4-(3-aminophenyl)indolin-2-one,
4-(2-aminophenyl)indolin-2-one,
there are obtained
2,3'-diamino-6-biphenylacetic acid,
2,2-diamino-6-biphenylacetic acid.

EXAMPLE 8

When in the procedure of Example 1, 2 moles of potassium hydroxide per mole of the phenylindolin-2-one is substituted for the sodium hydroxide, ethanol is substituted for water and 7-methyl-4-phenylindolin-2-one is replaced by equal molar amounts of
4-phenyl-5,7-diaminoindolin-2-one,
there is obtained
2,3,5-triamino-6-biphenylacetic acid.

EXAMPLE 9

When in the procedure of Example 1 and in the manner of the preceding discussion, 7-methyl-4-phenylindolin-2-one is replaced by equal molar amounts of
6-methyl-4-phenylindolin-2-one,
4-(3-chlorophenyl)indolin-2-one,
7-chloro-4-phenylindolin-2-one,
5,7-dichloro-4-phenylindolin-2-one,
there are obtained
2-amino-4-methyl-6-biphenylacetic acid,
2-amino-3'-chloro-6-biphenylacetic acid,
2-amino-3-chloro-6-biphenylacetic acid,
2-amino-3,5-dichloro-6-biphenylacetic acid.

EXAMPLE 10

Ethyl 2-Amino-6-biphenylacetate

Sodium 2-amino-6-biphenylacetate is dissolved in dimethylformamide and the solution treated with ethyliodide. The solution is stirred at room temperature for about 3 hours, the solution added to water and the mixture extracted several times with benzene. The combined benzene extracts are washed with dilute base and water, dried over sodium sulfate, concentrated under reduced pressure and crystallized to give ethyl 2-amino-6-biphenylacetate.

Formulation and Administration

The present invention also contemplates novel compositions containing the compounds of the present invention as active ingredients. Effective quantities of any of the foregoing pharmacologically active compounds may be administered to a living animal body in any one of various ways. For example, they may be orally administered in the form of sterile solutions. In forming the novel compositions of this invention, the active ingredient is incorporated in a suitable carrier such as a pharmaceutical carrier. Suitable pharmaceutical carriers which are useful in formulating the compositions of this invention include starch, gelatin, glucose, magnesium carbonate, lactose, malt and the like. Liquid compositions are also within the purview of this invention and suitable liquid pharmaceutical carriers include ethyl alcohol, propylene glycol, glycerine, glucose syrup and the like.

The pharmacologically active compounds of the present invention may be advantageously employed in a unit dosage of from about 1 to about 100 milligrams. The unit dosage may be given a suitable number of times daily so that the daily dosage may vary from 1 to 500 milligrams. Five to 50 milligrams appears to be an optimum unit dose.

It is only necessary that the active ingredient constitute an effective amount; i.e., such that a suitable effective dosage will be obtained consistent with the dosage form employed. The exact individual dosages as well as daily dosages will, of course, be determined according to standard medical principles under the direction of a physician or veterinarian.

The active agents of the present invention may be combined with other pharmacologically active agents, or with buffers, antacids or the like for administration. The proportion of the active agent in the compositions may be varied widely.

The following are examples of compositions formed in accordance with this invention.

1. Capsules

Capsules of 5 mg., 25 mg., and 50 mg. of active ingredient per capsule are prepared. With the higher amounts of active ingredient, adjustment may be made in the amount of lactose.

| Typical blend for encapsulation | Per Capsule mg. |
|---|---|
| Active ingredient | 5.0 |
| Lactose | 296.7 |
| Starch | 129.0 |
| Magnesium stearate | 4.3 |
| Total | 435.0 mg. |

Additional capsule formulations preferably contain a higher dosage of active ingredient and are as follows:

| Ingredients | Per Capsule mg. |
|---|---|
| Active ingredient | 25.0 |
| Lactose | 306.5 |
| Starch | 99.2 |
| Magnesium stearate | 4.3 |
| Total | 435.0 mg. |

In each case the selected active ingredient is uniformly blended with lactose, starch, and magnesium stearate and the blend encapsulated.

2. Tablets

A typical formulation for a tablet containing 5.0 mg. of active ingredient per tablet is as follows. The formulation may be used for other strengths of active ingredient by adjusting the weight of the dicalcium phosphate.

|  | Per tablet, mg. |
|---|---|
| (1) Active ingredient | 5.0 |
| (2) Corn starch | 13.6 |
| (3) Corn starch (paste) | 3.4 |
| (4) Lactose | 79.2 |
| (5) Dicalcium phosphate | 68.0 |
| (6) Calcium stearate | 0.9 |
|  | 170.1 mg. |

The tablets are formed by uniformly blending ingredients 1, 2, 4 and 5. Ingredient 3 is prepared as a 10 percent paste in water. The blend is granulated with starch paste and the resulting wet mass passed through an eight mesh screen. The wet granulation is dried and sized through a twelve mesh screen. The dried granules are blended with the calcium stearate and pressed.

3. Injectable—2% sterile solutions

|  | Per cc. |
|---|---|
| Active ingredient | 20 mg. |
| Preservative, e.g., chlorobutanol | 0.5% weight/volume |
| Water for injection | q.s. |

The solution is prepared, classified by filtration and placed into vials. The vials are sealed and heated in an autoclave.

Various modifications and equivalents will be apparent to one skilled in the art and may be made in the compounds, compositions, and methods of the present invention without departing from the spirit or scope thereof, and it is therefore understood that the invention is to be limited only by the scope of the appended claims.

What is claimed is:

1. A compound exhibiting muscle relaxant activity selected from the group having the formula:

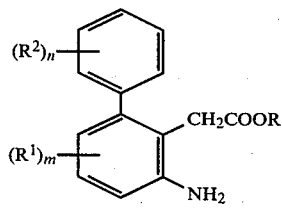

wherein;
R is hydrogen or lower alkyl,
$R^1$ is fluoro, chloro, bromo, lower alkyl or amino,
$R^2$ is lower alkyl, lower alkoxy, fluoro, chloro, bromo, amino or trifluoromethyl,
n is 0–3 and m is 0–2,
and the pharmaceutically acceptable salts thereof.

2. The compound of claim 1 in the form of a hydrate.

3. The compound of claim 1 wherein R is hydrogen, lower alkyl, sodium, or potassium.

4. 2-Amino-6-biphenylacetic acid or a pharmaceutically acceptable salt thereof.

5. A therapeutic composition suitable for providing muscle relaxation comprising (a) an effective amount of a compound selected from the group having the formula:

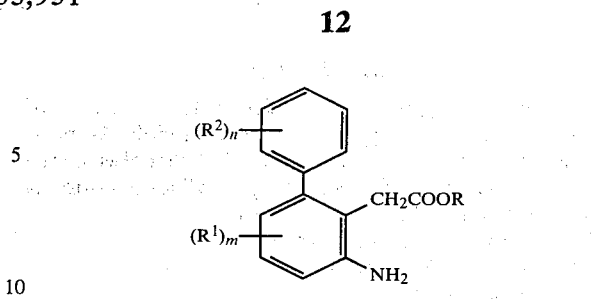

wherein;
R is hydrogen or lower alkyl,
$R^1$ is fluoro, chloro, bromo, lower alkyl or amino,
$R^2$ is lower alkyl, lower alkoxy, fluoro, chloro, bromo, amino or trifluoromethyl,
n is 0–3 and m is 0–2, and
the pharmaceutically acceptable salts thereof, and
(b) a pharmaceutically acceptable carrier therefor.

6. The composition of claim 5 wherein R is hydrogen, lower alkyl, sodium or potassium.

7. The composition of claim 5 wherein the effective amount ranges between about 1 and about 100 milligrams of said compound.

8. The composition of claim 5 wherein the compound is 2-amino-6-biphenylacetic acid or a pharmaceutically acceptable salt thereof.

9. A method for providing muscle relaxation in a living animal body with a minimum of undesirable side effects comprising internally administering to said living animal body an effective amount of a compound selected from the group having the formula:

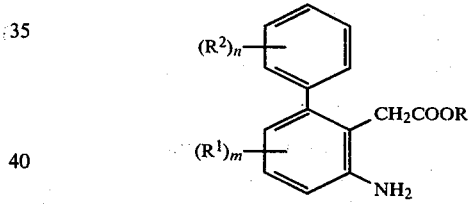

wherein;
R is hydrogen or lower alkyl,
$R^1$ is fluoro, chloro, bromo, lower alkyl or amino,
$R^2$ is lower alkyl, lower alkoxy, fluoro, chloro, bromo, amino or trifluoromethyl,
n is 0–3 and m is 0–2,
and the pharmaceutically acceptable salts thereof.

10. The method of claim 9 wherein R is hydrogen, lower alkyl, sodium or potassium.

11. The method of claim 9 wherein said effective amount ranges between about 1 and about 100 milligrams of said compound.

12. The method of claim 9 wherein the compound is 2-amino-6-biphenylacetic acid or a pharmaceutically acceptable salt thereof.

* * * * *